United States Patent [19]
Frehel et al.

[11] Patent Number: 5,534,530
[45] Date of Patent: Jul. 9, 1996

[54] 5-ACYLAMINO-1,2,4-THIADIAZOLES, THEIR PREPARATION AND PHARMACEUTICAL COMPOSITIONS CONTAINING THEM

[75] Inventors: Daniel Frehel, Toulouse; Danielle Gully, Saubens; Robert Boigegrain, Assas; Alain Badorc, Roquettes; Jean-Pierre Bras, Toulouse; Pierre Despeyroux, Labarthe s/Leze, all of France

[73] Assignee: Elf Sanofi, Paris, France

[21] Appl. No.: 226,862

[22] Filed: Apr. 13, 1994

[30] Foreign Application Priority Data

Apr. 16, 1993 [FR] France .................................. 93 04535

[51] Int. Cl.$^6$ ...................... C07D 285/12; A61K 31/41
[52] U.S. Cl. .................. 514/361; 514/294; 514/314; 546/95; 546/169; 548/128
[58] Field of Search ............. 548/128; 514/294, 514/314, 361; 546/95, 169

[56] References Cited

U.S. PATENT DOCUMENTS 5,189,049  2/1993  Frehel ..................................... 514/371

FOREIGN PATENT DOCUMENTS 0432040  6/1991  European Pat. Off. .
0518731  12/1992  European Pat. Off. .

OTHER PUBLICATIONS

Mylari, J. Med. Chem. 33 2019 (1990).

*Primary Examiner*—Robert Gerstl
*Attorney, Agent, or Firm*—Jacobson, Price, Holman & Stern

[57] ABSTRACT

The invention relates to thiadiazole derivatives corresponding to the general formula

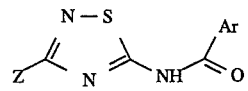

in which Ar represents a nitrogen-containing aromatic heterocycle, in particular indolyl which is substituted or unsubstituted on the nitrogen atom with $CO-(C_1-C_4)$alkyl; with $(CH_2)_nCOR$ in which n represents 1 or 2 and R represents $OR_1$ or $NR_1R_2$ with $R_1$ and $R_2$, which may be identical or different, representing H or $(C_1-C_4)$alkyl; with $(C_1-C_4)$ hydroxyalkyl; with $(C_2-C_6)$ alkoxyalkyl; tetrahydropyranyl; or with a $-(CH_2)_3-$ chain, the last carbon of which is attached to the phenyl ring of the indole to form a 6-membered ring;

Z represents (a) the group

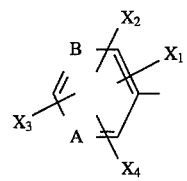

where A and B, independently of each other, represent C, CH or N; and $X_1$, $X_2$, $X_3$ and $X_4$, which may be identical or different, represent H, $(C_1-C_3)$alkyl, $(C_1-C_3)$alkoxy, Cl, Br or trifluoromethyl, or alternatively (b) an optionally substituted naphthyl group, as well as their pharmaceutically acceptable salts.

11 Claims, No Drawings

5-ACYLAMINO-1,2,4-THIADIAZOLES, THEIR PREPARATION AND PHARMACEUTICAL COMPOSITIONS CONTAINING THEM

The present invention relates to 5-acylamino-1,2,4-thiadiazoles, substituted in the 3 position with an aromatic group and linked by the carbonyl function to a nitrogen-containing aromatic heterocycle; these compounds have an affinity for biological cholecystokinin receptors.

Cholecystokinin (CCK) is a polypeptide hormone of which several fragments of 4 to 39 amino acids are found in vivo. They have many physiological activities, in particular on the bile system, the gastrointestinal tract or in the central and peripheral nervous system, as described by J. E. Morley in Life Sciences 30 479–493 (1982).

2 types of receptors, A and B, have been demonstrated, and the existence of other types or sub-types is not excluded. Agonists and antagonists of the action of cholecystokinin on these receptors are known; there may be mentioned the 3-eminobenzodiazepinone derivatives of J. Med. Chem. 32 13–16 (1989) or the 2-acylaminothiazole derivatives of EP-A-432,040 and EP-A-518,731, which, according to the nature of the substitutions, have a greater or lesser selectivity for the A or B type receptors.

Various antagonists and agonists of CCK are currently undergoing human clinical studies, in particular as appetite regulators, for treating gastrointestinal disorders, for the control of pain, for decreasing anxiety, in schizophrenia or for suppressing the withdrawal symptoms experienced by drug-dependent people.

The compounds of the invention which, owing to their structure, have an agonistic or antagonistic activity towards cholecystokinin on its A or B type receptors correspond to the formula

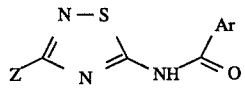

in which Ar represents a nitrogen-containing aromatic heterocycle chosen from quinolyl, isoquinolyl, benzimidazolyl and indolyl, the latter being optionally substituted on the nitrogen with a group W where W is chosen from (i) —CO—$(C_1-C_4)$alkyl;

(ii) —$(CH_2)_n$COR, where R represents $OR_1$ or $NR_1R_2$, $R_1$ and $R_2$, which may be identical or different, being chosen from H and $(C_1-C_4)$alkyl, and n is chosen from 1 and 2;

(iii) hydroxy $(C_1-C_4)$alkyl;

(iv) $(C_2-C_6)$alkoxyalkyl;

(v) tetrahydropyranyl;

(vi) a —$(CH_2)_3$— chain in which the last carbon is attached to the phenyl ring of the indole to form a 6-membered heterocycle;

Z represents

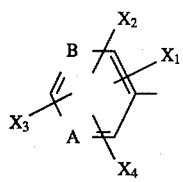

where A and B, independently of each other, represent C, CH or N; and $X_1$, $X_2$, $X_3$ and $X_4$, which may be identical or different, represent a hydrogen atom, a $(C_1-C_3)$ alkyl, $(C_1-C_3)$alkoxy, halo, in particular Cl or Br, or trifluoromethyl group; or alternatively (b) a naphthyl group which is optionally substituted with a $(C_1-C_3)$alkyl or $(C_1-C_3)$alkoxy group or a halogen atom.

The invention also relates to the pharmaceutically acceptable salts of the compounds of formula I.

Among these compounds, those are preferred in which at least 3 of the substituents $X_1$ to $X_4$ represent a hydrogen atom or a $(C_1-C_2)$alkyl or $(C_1-C_2)$alkoxy group and in particular those chosen from methyl or methoxy groups in the 2-, 4- or 6-position of the aromatic ring; moreover, it is preferred that Ar represents substituted or unsubstituted indolyl, and more particularly a substituted or unsubstituted 2-indolyl group.

The compounds of formula I may be prepared by condensation of an aminothiadiazole of formula II

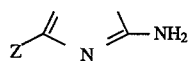

with an acid or a reactive derivative of an acid of formula Ar'COOH in which Ar' represents Ar or a derivative of Ar in which the functional groups which are sensitive under the usual acylation conditions will have been protected. Among the suitable acid derivatives which may be mentioned are acid chlorides, acid anhydrides and optionally mixed acid anhydrides, or the activated esters commonly used in peptide synthesis.

Some compounds of formula II are known; reference may for example be made to EP-A-455,356, or alternatively to DE 842,346 or DE 955,684, in which their preparation by the action of an alkali metal thiocyanate on the corresponding N-halo amidine is described. Other compounds of formula II are new and are prepared according to known methods. They may, for example, be obtained by the action of liquid ammonia on 5-chlorothiadiazole, which is suitably substituted in the 3 position, and which is obtained by the action of trichloromethanesulphenyl chloride on the suitably substituted amidine. The amidines are obtained by employing known methods, starting from the corresponding nitriles of formula III

or via the oxime which may be reduced to the amidine by hydrogen in the presence of a catalyst or via the imino ester which is treated with $NH_4Cl$.

All these reaction conditions are well known to a person skilled in the art.

When the nitriles are not commercially available, they may be prepared by the action of Lawesson's reagent on the corresponding primary amide, obtained from the carboxylic acid.

For the preparation of the acids Ar-COOH and their derivatives and the method of condensation with the amine, reference may be made to EP-A-432,040 and to DE-3,907, 390.

The compounds of the invention displace iodinated cholecystokinin or its iodinated biological fragments from its A- or B-type receptors.

The affinity for the A-type receptors has been studied in vitro on a rat pancreas homogenate, relative to iodinated 8 S CCK, according to the method described in particular in Endocrinology 109, 1746 (1981); under these conditions, the products described in the examples which follow have $IC_{50}$ values between $10^{-8}M$ and $10^{-10}M$.

The affinity for the B-type receptors has been studied by the method described in J. Neurochem. 37, 443 (1981); on a guinea-pig cortex homogenate the compounds of the examples have $IC_{50}$ values of the order of $10^{-7}M$.

Finally, in order to determine whether the compounds are agonists or antagonists on the A-type receptors, a person skilled in the art knows that he can study the action of the compounds on amylase secretion by rat pancreatic acini, according to a method described in particular in J. Biol. Chem 254 (12) 5321–5327 (1979); under these conditions, an agonist stimulates amylase secretion whereas an antagonist decreases the secretion induced by the 8 S CCK fragment. Among the compounds of formula I, those for which $X_1$, located in the 2-position, is $OCH_3$ and $X_2$ and $X_3$ are, independently of each other, methyl or methoxy are preferred agonist compounds.

On account of their tendency to displace cholecystokinin from its A or B receptors, the compounds of the invention may advantageously be used for the treatment or prevention of diseases in which cholecystokinin or its fragments are involved.

When these compounds are antagonists of CCK, they are used against ulcers, pancreas and spleen cancers, pancreatitis, hyperinsulinemia, irritable bowel syndrome or alternatively in psychosis, anxiety, Parkinson's disease, for decreasing tardive dyskinesia, as appetite regulators or in the treatment of pain or for combating the withdrawal symptoms experienced by drug-dependent people.

When these compounds are CCK agonists on the A-type receptors they are used as anorectic agents or alternatively in the treatment of psychosis, for improving the memory or relieving shock.

The pharmaceutical compositions which contain as active ingredient at least one compound of formula I or one of its pharmaceutically acceptable salts are another subject of the invention.

In the pharmaceutical compositions of the present invention for oral, sublingual, subcutaneous, intramuscular, intravenous, topical, intratracheal, intranasal, transdermic or rectal application, the active ingredients of formula I above, or of their optional salts, may be administered in single dosage administration forms, mixed with conventional pharmaceutical supports, to animals and to human beings for prophylaxis of or for treating the above disorders or diseases. Suitable single dosage forms of administration comprise forms via the oral route such as tablets, gelatine capsules, powders, granules and oral suspensions or solutions, sublingual, buccal, intratracheal or intranasal administration forms, subcutaneous, intramuscular or intravenous administration forms and rectal administration forms. For topical application, the compounds according to the invention may be used in creams, ointments or lotions.

When a solid composition is prepared in the form of tablets, the main active ingredient is mixed with a pharmaceutical vehicle such as gelatine, starch, lactose, magnesium stearate, talc, gum arabic or the like.

The tablets may be coated with sucrose, with a cellulose derivative or with other suitable materials or alternatively they may be treated such that they have a prolonged or delayed activity and so that they continuously release a predetermined amount of active ingredient.

A gelatine capsule preparation is obtained by mixing the active ingredient with a diluent and by pouring the mixture obtained into soft or hard gelatine capsules.

A preparation in the form of a syrup or elixir or for administration in drop form may contain the active ingredient together with a sweetener which is preferably non-calorific, methylparaben and propylparaben as antiseptic agent as well as a flavouring agent and a suitable colourant.

The water-dispersible powders or granules may contain the active ingredient mixed with dispersion agents or wetting agents, or suspension agents such as polyvinylpyrrolidone, and also with sweeteners or flavour adjusters.

For rectal administration, it is possible to have recourse to suppositories which are prepared with binders which melt at rectal temperature, for example cocoa butter or polyethylene glycols.

For parenteral administration, aqueous suspensions, isotonic saline solutions or sterile and injectable solutions are used which contain pharmacologically compatible dispersion agents and/or wetting agents, for example propylene glycol or burylens glycol.

The active ingredient may also be formulated in microcapsule form, optionally with one or more supports or additives.

The compositions of the present invention may contain, besides the products of formula I above or one of their pharmaceutically acceptable salts, other active ingredients which may be useful for treating the disorders or diseases indicated above.

The doses administered depend on the nature and the gravity of the disease, on the compound and on the route of administration. They will generally be between 20 and 100 mg per day orally in ]Human adults and 3 to 10 mg by injection.

Examples of preparation of example compounds of the invention are given in the description which follows.

EXAMPLE 1

2-[3-(2-Chlorophenyl)-1,2,4-thiadiazolyl-5-aminocarbonyl]-1-indoleacetic acid and its methyl ester.

Formula I:

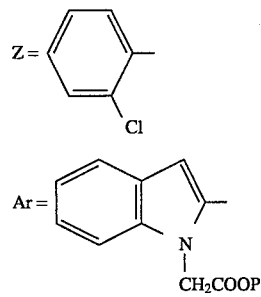

a) 2-Chlorobenzamidine 200 ml of methanol saturated with hydrogen chloride gas and 56 g of 2-chlorobenzonitrile are added together at a temperature in the region of 0° C. The mixture is maintained at +5° C. overnight (in a refrigerator). The reaction medium is subsequently evaporated without heating. The residue is taken up in 200 ml of dry methanol. The solution is cooled to a temperature in the region of 0° C. and ammonia gas is introduced thereto until a basic pH is obtained. The reaction medium is heated for 3 hours. After evaporating to dryness, the 2-chlorobenzamidine is purified by chromatography on a silica column (eluent: dichloromethane/methanol 8/2). M.p.=236° C. (hydrobromide) - Yield: 70%.

b) 5-Chloro-3-(2-chlorophenyl)-1,2,4-thiadiazole

To a mixture of 37 g of 2-chlorobenzamidine hydrobromide in 160 ml of dichloromethane, cooled to −10° C., are added dropwise 36 g of trichloromethanesulphenyl chloride dissolved in 160 ml of dichloromethane. After stirring for 30 min, 65 ml of aqueous 50% NaOH solution are added dropwise to the medium, still at −10° C. The solution is allowed to return to room temperature and is stirred for 2 h. Water is added to the reaction medium and the phases are separated after settling has taken place. The organic phase is washed with water, dried over sodium sulphate and evaporated to dryness.

c) 5-Amino-3-(2-chlorophenyl)-1,2,4-thiadiazole

The crystals obtained in the preceding step are suspended in an autoclave in 100 ml of methanol, and a large excess of liquid ammonia is added with cooling. The mixture is allowed to return to room temperature and stirring is carried out for 24 h before concentrating to dryness. The final product is purified by chromatography on a silica column (eluent: dichloromethane/hexane - 80/20).

M.p. = 136° C

Overall yield of steps b and c: 61%.

d) Methyl-2-[3-(2-chlorophenyl)-1,2,4-thiadiazolyl-5-aminocarbonyl]-1-indolylacetate 3.6 ml of pyridine are dissolved in 40 ml of dichloromethane and 0.90 ml of thionyl chloride is added at a temperature in the region of –5° C. The mixture is left for 30 min at –5° C. and 3 g of 1-(methoxycarbonylmethyl)-2-indolecarboxylic acid are added portionwise. Stirring is carried out for 30 min at the same temperature, followed by portionwise addition of 2.4 g of 5-amino-3-(2-chlorophenyl)-1,2,4-thiadiazole. The mixture is allowed to return to room temperature and is stirred for 18 hours. The reaction medium is washed with water and, after separation of the solution phases by settling, the organic phase is dried over sodium sulphate and evaporated to dryness. The product is purified by chromatography on a silica column (eluent: dichloromethane/methanol - 95/5), and then recrystallized in isopropyl ether.

M.p.=197° C. - Yield 69%.

e) 2-[3-(2-Chlorophenyl)-1,2,4-thiadiazolyl-5-aminocarbonyl]-1-indoleacetic acid 1 g of methyl 2-[3-(2-chlorophenyl)-1,2, 4-thiadiazolyl-5-aminocarbonyl]-1-indolylacetate is suspended in 20 ml of methanol and 7 ml of aqueous 1N NaOH solution are added at room temperature. The mixture is stirred at room temperature for 3 hours; the reaction medium is concentrated; water is added thereto and the pH is adjusted to 3 by addition of KHSO$_4$. The precipitate is isolated.

M.p.=255° C. - Yield: 92%.

EXAMPLE 2

2-[3-(2,4,6-Trimethoxyphenyl)-1,2,4-thiadiazolyl-5-aminocarbonyl]-1-indoleacetic acid and its methyl ester.

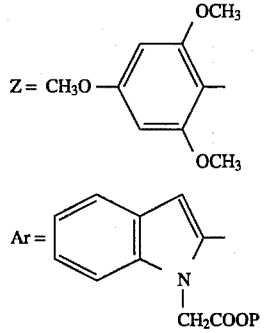

a) 2,4,6-Trimethoxybenzamidoxime

To a suspension of 13.8 g of hydroxylamine hydrochloride in 100 ml of ethanol is added, at a temperature in the region of 15° C., a solution of NaOC$_2$H$_5$ prepared by dissolving 4.3 g of sodium in 100 ml of ethanol. 12 g of 2,4,6-trimethoxybenzonitrile are introduced into the medium, followed by heating at reflux for 41 h before evaporating to dryness. The crystals are washed with water and with dichloromethane.

M.p. 205° C.; Yield: 71%.

b) 2,4,6-Trimethoxybenzamidine 3.4 g of 2,4,6-trimethoxybenzamidoxime are dissolved in 120 ml of a methanol/dichloromethane/acetic acid mixture (2/2/1; (v/v/v)) in an autoclave and hydrogenation is carried out at a pressure of 2×10$^6$ Pa in the presence of 1 g of Raney nickel. After hydrogenation for 2 hours, the catalyst is separated out and the mixture is concentrated to dryness.

c) 5-Chloro-3-(2,4,6-trimethoxyphenyl)-1,2,4-thiadiazole

The resin obtained in the preceding step is dissolved in 20 ml of dichloromethane, cooled to –10° C., and 2.8 ml of trichloromethanesulphenyl chloride dissolved in 20 ml of dichloromethane are added dropwise. The reaction medium is stirred for 30 minutes at –10° C. and 5 ml of aqueous 30% NaOH solution are added dropwise, and the reaction medium is subsequently stirred for 2 hours at room temperature before adding water; after separation of the phases by settling the organic phase is washed with water, dried over sodium sulphate and evaporated to dryness.

d) 5-Amino-3-(2,4,6-trimethoxyphenyl)-1,2,4-thiadiazole

The crystals obtained in the preceding step are suspended in 100 ml of methanol in an autoclave and a large excess of liquid ammonia is added with cooling. The mixture is allowed to return to room temperature and is stirred for 18 hours before evaporating to dryness. 100 ml of aqueous 2N hydrochloric acid solution are added to the residue; the precipitate formed is filtered off and washed with water and then with acetone.

M.p.=215° C. (hydrochloride); Overall yield for the 3 steps: 41%.

e) Methyl 2-[3-(2,4,6-trimethoxyphenyl)- 1,2,4-thiadiazolyl-5-aminocarbonyl]-1-indolylacetate 1.5 ml of pyrridine are dissolved in 20 ml of dichloromethane and 0.34 ml of thionyl chloride is added at a temperature in the region of –5° C. The mixture is left for 30 minutes at –5° C. and 1 g of 1-(methoxycarbonylmethyl)-2-indolecarboxylic acid is added portionwise. The mixture is stirred for 30 minutes at the same temperature, followed by portionwise addition of 1.24 g of 5-amino-3-(2,4,6-trimethoxyphenyl)-1,2,4-thiadiazole hydrochloride; the mixture is allowed to return to room temperature and then stirred for 18 hours. The reaction medium is washed with water. After separation of the phases after settling has taken place, the organic phase is dried over sodium, sulphate and evaporated to dryness. The final product is purified by chromatography on a silica column (eluent: dichloromethane/methanol - 95/5) and is crystallized in isopropyl ether.

M.p.=205° C. - Yield: 78%.

f) 2-[3-(2,4,6- Trimethoxyphenyl)-1,2,4-thiadiazolyl-5-aminocarbonyl]-1-indoleacetic acid 0.7 g of methyl 2-[3-(2,4,6-trimethoxyphenyl)-1,2, 4-thiadiazolyl-5-aminocarbonyl]-1-indoleacetate is suspended in 15 ml of methanol and 4.4 ml of aqueous 1N NaOH solution are added at room temperature. The solution is stirred at room temperature for 3 hours. The reaction medium is evaporated. Water is added and the pH is brought to 3 by addition of KHSO$_4$. The precipitate formed is isolated.

M.p.=260° C. - Yield: 65%.

EXAMPLE 3

2-[3-(2,6-Dimethoxy-4-methylphenyl)- 1,2,4-thiadiazolyl-5-aminocarbonyl]-1-indoleacetic acid and its methyl ester.

Formula I:

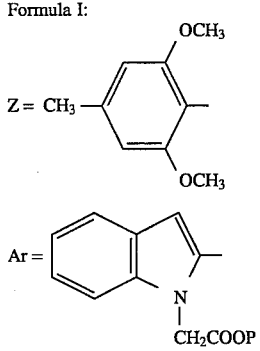

a) 2,6-Dimethoxy-4-methylbenzoic acid 104 ml of 1.6M n-butyllithium solution in hexane are added to 200 ml of tetrahydrofuran, followed by dropwise addition of 25 ml of 3,5-dimethoxytoluene, at a temperature between 0° and 5° C. The reaction medium is stirred at 5° C. for 1 h 30, followed by introduction of excess gaseous $CO_2$ over 30 minutes. The mixture is introduced into 200 ml of aqueous 0.5N HCl solution and the aqueous phase is extracted with ethyl acetate. The residue is concentrated and chromatographied on a silica column (eluent: dichloromethane/methanol - 93/7).
M.p.=178° C.; Yield: 72%.

b) 2,6-Dimethoxy-4-methylbenzamide 7 g of the above acid are dissolved in 100 ml of dichloromethane and 6.7 ml of oxalyl chloride are added dropwise to the solution, while maintaining the temperature at 10° C. The mixture is left for 4 hours at room temperature before evaporating to dryness; 100 ml of liquid ammonia are poured onto the residue and the mixture is left at 20° C. for 18 hours in an autoclave. After evaporating to dryness, a mixture of water and ethyl acetate is poured onto the residue and the final product is extracted in the organic phase. The product is purified by chromatography on a silica column (eluent: dichloromethane/methanol - 9/1).
M.p.=201° C.; Yield: 73%.

c) 2,6-Dimethoxy-4-methylbenzonitrile 3 g of the above amide are suspended in 60 ml of toluene and 3.7 g of Lawesson's reagent are added before heating the mixture at 90° C. for 1 h 30. The reaction medium is evaporated to dryness and the residue is taken up in ethyl acetate; the organic solution is washed with aqueous NaOH solution, dried and concentrated. The residue is purified by chromatography on a silica column (eluent:dichloromethane/toluene - 1/1).
M.p.=122° C.; Yield: 92%.

d) 2,6-Dimethoxy-4-methylbenzamidoxime

To a solution of 2.6 g of the above benzonitrile in 30 ml of ethanol are added 2.2 g of hydroxylamine hydrochloride and then 1.34 g of NaOH pellets. The reaction medium is brought to reflux for 48 hours and then evaporated to dryness. The residue is taken up in 100 ml of aqueous 1N HCl solution and washed with ethyl acetate; the solution is brought to pH 5 by addition of aqueous 1N NaOH solution and the amidoxime hydrochloride is then extracted in ethyl acetate.
M.p.=140° C.; Yield: 75%.

e) 5-Amino-3-(2,6-dimethoxy-4-methylphenyl)-1,2,4-thiadiazole 3.2 g of 2,6-dimethoxy-4-methylbenzamidoxime dissolved in 50 ml of methanol are introduced into an autoclave and 400 mg of Raney Ni are added; hydrogenation is carried out at 20° C. at a pressure of $1.4 \times 10^6$ Pa of hydrogen for 12 hours. The catalyst is filtered off on a bed of talc and the methanolic filtrate is evaporated to dryness. The residual yellow oil is dissolved in 50 ml of dichloromethane and 2.84 g of trichloromethanesulphenyl chloride are added at 20° C., followed by dropwise addition at −10° C. of a solution of 3 g of NaOH in 20 ml of water. The mixture is allowed to return to 20° C. at the end of the addition and is stirred for 3 hours. The desired product is then extracted from the reaction medium with dichloromethane. This oil is dissolved in a mixture of 40 ml of methanol and 10 ml of dichloromethane and it is introduced, after cooling, into an autoclave containing 200 ml of liquid ammonia; after 12 hours at room temperature, the residue is concentrated and taken up in $CH_2Cl_2$; the organic phase is washed with water and concentrated, and the final product is purified by chromatography on a silica column (eluent: dichloromethane/methanol - 96/4).
M.p.=117° C. - Overall yield: 58%.

f) Methyl 2-[3-(2,6-dimethoxy-4-methylphenyl)-1,2,4-thiadiazolyl-5-aminocarbonyl]-1-indolylacetate 1 ml of pyridine is introduced into 10 ml of dichloromethane at 0° C., followed by 0.25 ml of thionyl chloride; after 30 min, 0.2 g of 1-(methoxycarbonylmethyl)-2-indolecarboxylic acid chloride is added portionwise to the reaction medium, followed by dropwise addition of 0.8 g of 5-amino-3-(2,6-dimethoxy-4-methylphenyl)-1,2,4-thiadiazole dissolved in 10 ml of dichloromethane. The mixture is left for 5 hours at 20° C. before introducing one volume of water thereto. The organic phase is separated from the mixture, it is dried and the solvent is evaporated off. The yellow oil obtained is purified by chromatography on a silica column (eluent: dichloromethane/diethyl ether - 95/5). The product is recrystallized in isopropanol.
M.p.=122° C.; Yield: 65%.

g) 2-[3-(2,6-Dimethoxy-4-methylphenyl)-1,2, 4-thiadiazolyl-5-aminocarbonyl]-1-indoleacetic acid 0.35 g of the above methyl ester is introduced into 5 ml of methanol, followed b3, 1.5 ml of aqueous 1N NaOH solution. After stirring for 6 hours, the methanol is evaporated off, 50 ml of water are poured onto the residue and the medium is acidified with aqueous 5% (weight/volume) $KHSO_4$ solution. The aqueous phase is extracted with dichloromethane and the organic phase is concentrated. The product is obtained in the form of yellow crystals.
M.p.=235° C.; Yield: 82%.

EXAMPLE 4

N-[3-(2,6-Dimethoxy-4-methylphenyl)-1,2,4-thiadiazol-5-yl]-1-(2-tetrahydropyranyl)-2-indolyl carboxamide Formula I:

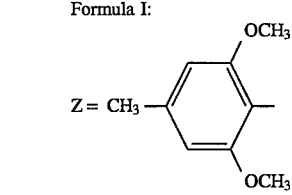

Ar = 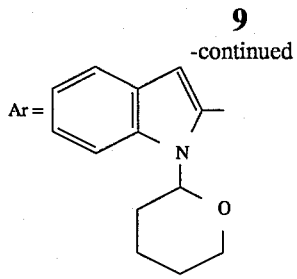

1.8 ml of pyridine are introduced into 20 ml of dichloromethane. The mixture is brought to 0° C. and 0.36 ml of thionyl chloride is added thereto. After 30 minutes, 1.2 g of 1-(2-tetrahydropyranyl)-2-indolecarboxylic acid chloride are introduced portionwise, followed by dropwise addition of 1.2 g of 5-amino-3-(2,6-dimethoxy-4-methylphenyl)-1,2,4-thiadiazole dissolved in 10 ml of dichloromethane. After 3 hours at −20° C., one volume of water is introduced into the reaction medium and the aqueous phase is extracted with dichloromethane. The organic phases are subsequently dried and concentrated. The residue is purified by chromatography on a silica column (eluent: dichloromethane/methanol - 99/1).
M.p.=142° C.; Yield=80%.

EXAMPLE 5

N-[3-(2-Chlorophenyl)-1,2,4-thiadiazol-5-yl]-1(2-tetrahydropyranyl)-2-indolylcarboxamide Formula I:

Z = 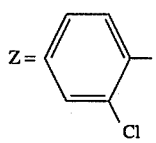

Ar = 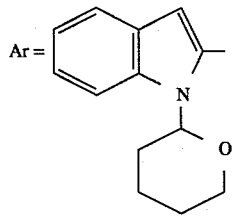

prepared as in Example 4, starting from 5-amino-3-(2-chlorophenyl)-1,2,4-thiadiazole, which melts at 136° C.
M.p.=182° C.; Yield: 90%.

EXAMPLE 6

N-[3-(2,6-Dimethoxy-4-methylphenyl)- 1,2,4-thiadiazol-5-yl]-2-indolylcarboxamide Formula I:

Z = CH$_3$ 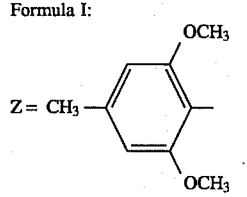

Ar = 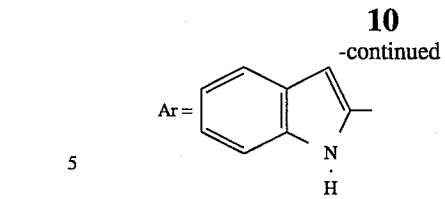

0.4 g of the compound of Example 4 is dissolved in 25 ml of methanol and 0.8 ml of aqueous 6N HCl solution is added. The reflux temperature is maintained for 6 hours, followed by evaporation of the solvent; the final product is extracted from the aqueous medium into dichloromethane.
M.p.=247° C. - Yield 94%.

EXAMPLE 7

N-[3-(2-Chlorophenyl)-1,2,4-thiadiazol-5-yl]-2-indolylcarboxamide

Formula I:

Z = 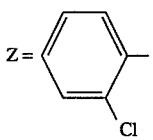

Ar = 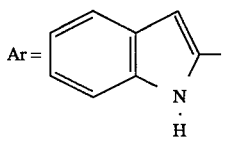

prepared as in Example 6, starting from the compound of Example 5.
M.p.=291° C. - Yield: 86%.

EXAMPLE 8

N-[3-(2-Chlorophenyl)-1,2,4-thiadiazol-5-yl]-2-quinolinecarboxamide

Formula I:

Z = 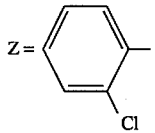

Ar = 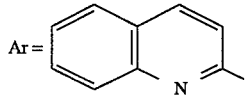

By using the procedure of Example 1 and starting from the appropriate carboxylic acid, the title compound was obtained.
M.p.=114° C. - Yield: 85%.

EXAMPLE 9

N-[3-(2-Chlorophenyl)-1,2,4-thiadiazol-5-yl]-5,6-dihydro-4H-pyrrolo [3,2,1-ij]quinoline-2-carboxamide Formula I:

Z = 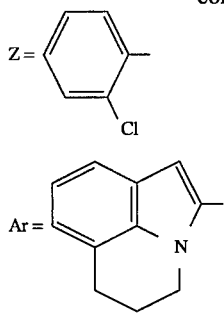

Ar = (indole with propyl chain)

By using the procedure of Example 1 and starting from the appropriate carboxylic acid, the title compound was obtained.

M.p.=195° C. - Yield: 79%.

By performing the process according to Examples 1 to 9 above, the compounds of formula I of Examples 10 to 21 listed in the following Table I are prepared. The 5-amino-1,2,4-thiadiazole intermediates P1 to P4 leading to the compounds of Examples 10 to 21 are reported in the following Table II.

TABLE I (I) Structure: N=S-N=C(Z)-NH-C(O)-[indole-N-W]

| Example number | Z | W | M.p.; °C. |
|---|---|---|---|
| 10 | 2,4,5-tri(OCH₃)-phenyl | tetrahydropyran-2-yl | 214 |
| 11 | 4-OCH₃-2-CH₃-5-OCH₃-phenyl (H₃CO, H₃C, OCH₃) | tetrahydropyran-2-yl | 226 |
| 12 | 4-OCH₃-2-CH₃-5-OCH₃-phenyl | —CH₂COOCH₃ | 212.5 |
| 13 | 2-OCH₃-4-CH₃-5-OCH₃-phenyl | —CH₂COOH | 212 |
| 14 | 2-OCH₃-4-CH₃-5-OCH₃-phenyl | H | 255 |
| 15 | 2-OCH₃-4-CF₃-6-OCH₃-phenyl | —CH₂COOCH₃ | 262 |
| 16 | 2-OCH₃-4-CF₃-6-OCH₃-phenyl | H | 168 |
| 17 | 2,4,5-tri(OCH₃)-phenyl | —CH₂COOCH₃ | 178 |
| 18 | 2,4,5-tri(OCH₃)-phenyl | —CH₂COOH | 214 |
| 19 | 2-OCH₃-4-CF₃-6-OCH₃-phenyl | tetrahydropyran-2-yl | 283 |
| 20 | 2-naphthyl | —CH₂COOCH₃ | 236 |
| 21 | 2-naphthyl | —CH₂COOH | 283 |

TABLE II (II)

| Compound number | Z | M.p.; °C. |
|---|---|---|
| P1 | 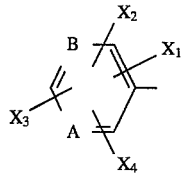 (2,4,5-trimethoxy with OCH₃ groups) | 233 |
| P2 | 2,5-dimethoxy-4-methyl phenyl | 195 |
| P3 | 2,6-dimethoxy-4-trifluoromethyl phenyl | 198 |
| P4 | 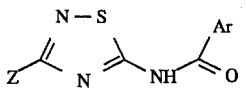 naphthyl | 153 |

We claim:

1. A compound of formula I

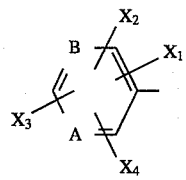

in which Ar represents a nitrogen-containing aromatic heterocycle selected from quinolyl, isoquinolyl, benzimidazolyl, indolyl, indolyl substituted on the nitrogen with a group W where W is selected from (i) —CO—$(C_1-C_4)$alkyl;

(ii) —$(CH_2)_n$COR, where n represents 1 or 2 and R is selected from $OR_1$ and $NR_1R_2$, $R_1$ and $R_2$ which may be identical or different, being selected from H and $(C_1-C_4)$ alkyl;

(iii) hydroxy$(C_1-C_4)$alkyl;

(iv) $(C_2-C_6)$alkoxyalkyl;

(v) tetrahydropyranyl;

(vi) a —$(CH_2)_3$-chain in which the last carbon is attached to the phenyl ring of the indole to form a 6-membered heterocycle; Z is selected from (a) and (b), where (a) is the group where A and B are independently selected from C, CH and N; and $X_1$, $X_2$, $X_3$ and $X_4$, which may be identical or different, are independently selected from hydrogen, chlorine, bromine, $(C_1-C_3)$alkyl, $(C_1-C_3)$alkoxy and trifluoromethyl; and (b) is selected from naphtyl and naphtyl substituted with a group selected from $(C_1-C_3)$alkyl, $(C_1-C_3)$alkoxy and halogen as well as its pharmaceutically acceptable salts.

2. A compound of formula I according to claim 1, in which at least 3 of the groups $X_1$, $X_2$, $X_3$ and $X_4$, which may be identical or different, are selected from hydrogen, $(C_1-C_2)$alkyl and $(C_1-C_2)$alkoxy.

3. A compound of formula I according to claim 1, in which the groups $X_1$, $X_2$ and $X_3$ are located in the 2-, 4- and 6-position of the aromatic ring and are selected from methyl and methoxy.

4. A compound of formula I according to claim 1, in which Ar is selected from 2-indolyl and 2-indolyl substituted on the nitrogen with a group W where W is selected from (i) —CO—$(C_1-C_4)$alkyl;

(ii) —$(CH_2)_n$, where n is selected from 1 and 2 and R is selected from $OR_1$ and $NR_1R_2$, $R_1$ and $R_2$, which may be identical or different, being selected from H and $(C_1-C_4)$alkyl;

(iii) hydroxy$(C_1-C_4)$alkyl;

(iv) $(C_2-C_6)$alkoxyalkyl;

(v) tetrahydropyranyl;

(vi) a —$(CH_2)_3$-chain in which the last carbon is attached to the phenyl ring of the indole to form a 6-membered heterocycle.

5. A compound of formula I according to claim 1, in which $X_1$, located in the 2-position, represents methoxy and $X_2$ and $X_3$ are, independently of each other selected from methyl and methoxy.

6. A compound of formula I according to claim 1, in which Ar represents a nitrogen-containing aromatic heterocycle selected from quinoline, isoquinoline, benzimidazole and indole, it being possible for the said indole group to be substituted on the nitrogen with a group selected from CO—$(C_1-C_4)$alkyl; $CH_2$COR in which R is selected from $OR_1$ and $NR_1R_2$ with $R_1$ and $R_2$, which may be identical or different, being selected from H and $(C_1-C_4)$alkyl; $C_1$ to $C_4$ hydroxyalkyl; $C_2$ to $C_6$ alkoxyalkyl; tetrahydropyranyl; and a —$(CH_2)_3$— chain, the last carbon of which is attached to the phenyl ring of the indole to form a 6-membered ring; Z represents the group where A and B, independently of each other, are selected from C, CH and N; and $X_1$, $X_2$, $X_3$ and $X_4$, which may be identical or different, are selected from H, $(C_1-C_3)$alkyl, $(C_1-C_3)$alkoxy, Cl, Br and trifluoromethyl, as well as its pharmaceutically acceptable salts.

7. A pharmacological composition comprising an effective amount of a CCK antagonist or agonist compound according to claim 2 combined with a pharmaceutical vehicle.

8. A pharmacological composition comprising an effective amount of a CCK antagonist or agonist compound according to claim 3 combined with a pharmaceutical vehicle.

9. A pharmacological composition comprising an effective amount of a CCK antagonist or agonist compound according to claim 4 combined with a pharmaceutical vehicle.

10. A pharmacological composition comprising an effective amount of a CCK antagonist or agonist compound according to claim 5 combined with a pharmaceutical vehicle.

11. A pharmacological composition comprising an effective amount of a CCK antagonist or agonist compound according to claim 8 combined with a pharmaceutical vehicle.

* * * * *